United States Patent [19]

Guinn

[11] Patent Number: 5,907,035
[45] Date of Patent: May 25, 1999

[54] AQUEOUS TWO-PHASE METAL AFFINITY PARTITIONING PROTEIN PURIFICATION SYSTEM

[75] Inventor: Martin R. Guinn, Boulder, Colo.

[73] Assignee: Baxter Biotech Technology Sárl, Neuchatel, Switzerland

[21] Appl. No.: 08/861,587

[22] Filed: May 22, 1997

Related U.S. Application Data

[60] Provisional application No. 60/018,212, May 23, 1996.

[51] Int. Cl.$^6$ .......................... A61K 35/14; C07K 14/00; C07K 16/00; C07K 17/00
[52] U.S. Cl. ........................... 530/412; 530/380; 530/385
[58] Field of Search ................................ 530/344, 385, 530/380, 412

[56] References Cited

U.S. PATENT DOCUMENTS 5,407,579   4/1995   Lee et al. ................................. 530/385

OTHER PUBLICATIONS

Krishnamurthy et al./Conditions Promoting Metal–Catalyzed Oxidations During Immobilized Cu–Iminodiacetic Acid Metal Affinity Chromatography/Biotechnol. Prog. (1995) 11:643–650.

Chung & Arnold/Metal–Affinity Partitioning of Phosphoproteins in Peg/Dextran Two–Phase Systems/Biotechnology Ltrs. (1991) 13(8):615–620.

Wuenschell et al/Aqueous Two–Phase MEtal Affinity Extraction of Heme Proteins/Bioprocess Engineering (1990) 5: 199–202.

Porath et al./Metal Chelate Affinity Chromatography, A New Approach to Protein Fractionation/Nature (1975) 258:598–599.

Johanson/Partitioning in Aqueous Two–Phase Systems, Theory, Methods, Uses, and and applications to Biotechnology/Partitioning of Proteins/(1985) Chapter 6/161–226/ED. Walter, Brooks, Fisher/Academic Press, Inc.

Birkenmeier et al/Immobilized Metal Ion Affinity Partitioning, A Method Combining Metal–Protein Interaction and Partitioning of Proteins in Aqueous Two–Phase Systems/J of Chrom. (1991) 539:267–277.

Todd et al./Cu(II)–Binding Properties of a Cytochrome c With a Synthetic Metal–Binding Site: HIS–$X_3$–HIS in an α–Helix/Proteins: Structure, Function, and Genetics (1991) 10:156–161.

Plunkett et al./Metal Affinity Extraction of Human Hemoglobin in an Aqueous Polyethylene Glycol–Sodium Sulfate Two–Phase System/Biotech. Tech. (1990) 4(1):45–48.

Hart & Bailey/Purification and Aqueous Two–Phase Partitioning Properties of Recombinant Vitreoscilla Hemoglobin/Enzyme Micron. Technol. (1991) 13: 788–795.

*Primary Examiner*—Cecilia J. Tsang
*Assistant Examiner*—S. G. Marshall
*Attorney, Agent, or Firm*—Senniger, Powers, Leavitt & Roedel

[57] ABSTRACT

The present invention relates to methods of purifying proteins having surface active, electron-rich amino acids using an aqueous two phase system. The methods include the use of salts and inert hydrophobic molecules, such as polymers, to produce the aqueous two phase system and the use a polymer-chelator-metal complex to purify the target proteins.

28 Claims, No Drawings

AQUEOUS TWO-PHASE METAL AFFINITY PARTITIONING PROTEIN PURIFICATION SYSTEM

This application claims the benefit of U.S. Provisional Application No. 60/018212 filed May 23, 1996.

FIELD OF THE INVENTION

This invention relates to novel methods of protein purification using, among other things, aqueous two-phase metal affinity partitioning.

BACKGROUND OF THE INVENTION

Metal affinity partitioning (Johansson, G. 1985. Partitioning of proteins, pp. 161–219. In: H. Walter, D. E. Brooks, and D. Fisher (eds.), Partitioning in aqueous two-phase systems. Academic Press, Orlando) exploits the affinity of transition metal ions for electron-rich amino acid residues, such as histidine and cysteine, accessible on the surfaces of some proteins. When the metal ion is partially chelated and coupled to a linear polymer, such as polyethylene glycol ("PEG"), the resulting polymer-bound metal chelate can be used to enhance the partitioning of metal binding proteins into the polymer-rich phase of a PEG-salt or PEG-dextran aqueous two-phase system. Since most proteins favor the salt-rich heavy phase of an aqueous two-phase system, metal affinity partitioning may be a very efficient and selective means of isolating and purifying a metal-binding protein from a crude mixture, although, prior to the instant invention, this was not done.

The application of a metal affinity ligand for the isolation of proteins is set forth in Porath, et al. (Porath, J., Carlsson, J., Olsson, L., Belfrage, G. 1975. Nature 258:598–599) who demonstrated that histidine- and cysteine-containing proteins could be chromatographically separated from each other using a support that had been functionalized with a chelator, such as iminodiacetic acid ("IDA"), which is attached to a polymer spacer and bound to a metal such as copper, zinc or nickel. Immobilized metal affinity chromatography ("IMAC") has evolved into a very powerful tool for protein chromatography and a number of IDA-based IMAC resins are now commercially available (Sulkowski, E. 1985. Purification of proteins by IMAC. Trends Biotechnol. 3:1–7).

Metal affinity partitioning of previously purified proteins has been reported by Wuenschell, et al. (Wuenschell, G. E., Naranjo, E., Arnold, F. H. 1990. Bioprocess Eng. 5:199–202) who studied the partitioning of selected purified heme-containing proteins in an aqueous two-phase system of PEG and dextran using Cu(II)IDA-PEG as the affinity ligand. They showed that protein partitioning was affected by the number of accessible histidine residues on the protein surface.

Birkenmeier, et al. (Birkenmeier, G., Vijayalakshmi, M. A., Stigbrand, T., Kopperschlager, G. 1991. J. Chrom. 539:267–277) investigated the relative affinities of several transition metal ions by comparing the partitioning of purified $\alpha_2$-macroglobulin, tissue plasminogen activator, superoxide dismutase, and monoclonal antibodies using IDA-PEG chelated with Cu(II), Ni(II), Zn(II) and Fe(III) in an aqueous two-phase system of PEG and dextran. Their findings suggested that copper is the most effective transition metal ion for metal affinity partitioning. However, the use of copper may be problematical. Cu(II)-catalyzed oxidation of heme-proteins has been well-characterized by Rifkind (Rifkind, J. M., 1974. Biochemistry, 13:2475–2481) who showed that, in the absence of a strong chelator such as EDTA, autoxidation of heme proteins occurs rapidly, within 1–3 minutes, with as little as $10^{-3}$ molar equivalents of Cu(II). Hemoglobin undergoes rapid oxidation by Cu(II) but is unaffected by Ni(II), Zn(II) and other common transition metal ions. Heme oxidation is initiated by the binding of Cu(II) to a high affinity copper binding site followed by the dissociation of the sixth liganded position of the heme (Rifkind, JM 1976. Biochemistry 15: 5337–5343). Oxidation of the heme iron from Fe(II) to Fe(III) can result in an irreversible loss of oxygen binding ability. Furthermore, unchelated Cu(II) in a protein solution can cause protein precipitation (Nagel, R. L., Bemski, G., Pincus, P., 1970. Arch. Biochem. Biophys. 137: 428–434). Metal catalyzed oxidation ("MCO") reactions during immobilized metal affinity chromatography with Cu(II)IDA-linked resins have been recently reported (Krishnamurthy, R., Madurawe, R. D., Bush, K. D., Lumpkin, J. A. 1995. Biotechnol. Prog. 11:643–650).

Protein partitioning has been shown by Suh and Arnold (Suh, S.-S., Arnold, F. H. 1990. Biotechnol. Bioeng. 35:682–690) to depend on ligand concentration, pH, number and $pK_a$ of accessible surface histidines, and the association constant for the binding of the metal ligand to the unprotonated histidine side chains. They used these observations to develop a comprehensive model for metal affinity partitioning. Arnold and her coworkers have partitioned other purified proteins using IDA-PEG including recrystallized human hemoglobin with Cu(II)IDA-PEG as the metal ligand (Plunkett, S. D., Arnold, F. H. 1990. Biotechnol. Tech. 4:45–48) and phosphoproteins, such as egg yolk phosvitin, with Fe(III) IDA-PEG as the metal ligand (Chung, B. H., Arnold, F. H. 1991. Biotechnol. Let. 13:615–620).

Enhanced partitioning of a protein also depends on the spatial arrangement of electron-rich amino acid residues on the protein surface. For example, two histidines separated by three amino acids on an $\alpha$-helix exhibit a particularly high metal binding affinity (Sulkowski, E. 1987. pp. 149–162. In Protein purification: micro to macro, R. Burgess (ed.), A. R. Liss, Inc. New York). Metal binding sites containing the His-$X_3$-His motif have been engineered onto the surface of iso-1-cytochrome c (Todd, R. J., Van Dam, M. E., Casimiro, D., Haymore, B. L., Arnold, F. H. 1991. Proteins: Structure, Function, and Genetics 10:156–161) and into hirudin (Chung, B. H., Sohn, J. H., Rhee, S.-K., Chang, Y. K., Park, Y. H. 1994. J. Ferm. Bioeng. 77:75–79) a 65-amino acid peptide, to enhance partitioning with Cu(II)IDA-PEG in aqueous two-phase systems. All of the studies listed above involved single-protein partitioning using protein that was previously isolated and purified by conventional methods.

While the ability of metal chelates to recognize and partition metal-binding proteins has been well-documented in artificial settings such as those described above, development of metal affinity partitioning into a useful technology for the isolation and purification of proteins from crude solutions was not done prior to the present invention. There are many problems to overcome in using metal chelates to purify a target protein from a crude preparation. In particular with heme-containing proteins, there is the oxidation problem referred to above and the question of how selective the ligand is for the target protein. There also is a problem of nitrogen-containing compounds in the crude system inhibiting ligand binding to the target protein. Finally, there is a problem relating to protein solubility and potential precipitation of proteins by the salt used in an aqueous two-phase partitioning system. Applicant has overcome these and other problems to develop a functional aqueous two-phase metal affinity partitioning system for purifying target proteins from crude protein solutions.

SUMMARY OF THE INVENTION

The present invention relates to methods for purifying target proteins from initially crude protein solutions.

More specifically, the present invention relates to methods of purifying proteins, particularly proteins having electron-rich amino acids, particularly histidine, on the protein surface ("target protein(s)"), from crude or partially purified protein solutions, using aqueous two-phase systems.

Even more particularly, the invention relates to the use of metal affinity partitioning to purify such proteins using such aqueous systems.

Even more particularly, the methods involve the use of polyethylene glycol, or similar inert hydrophobic molecules, conjugated to a metal chelator such as IDA, which is charged with a divalent metal ligand such as copper, and contacting the PEG-chelator-metal complex with a crude protein solution containing a target protein, thereby causing the PEG-chelator-metal complex to bind the target protein, which complex-target protein combination is then partitioned to the inert hydrophobic molecule phase of a two-phase aqueous solution comprising an inert hydrophobic molecule and a salt.

The PEG-chelator-metal complex may be added directly to a crude protein solution containing the target protein. Salts and PEG may then be added to the crude protein solution containing the PEG-chelator-metal complex and the solution allowed to form the two-phase system. Purified protein can be collected from the appropriate phase, or solid debris can be removed from the relevant phase leaving the purified protein.

Alternatively, the crude solution may first be clarified, or subject to several partitioning steps using a two-phase aqueous system comprising an inert hydrophobic molecule and a salt, prior to adding the PEG-chelator-metal complex.

Even more particularly, the process may, for example, involve the following steps:

1. Cells containing the target protein are lysed;
2. salt and inert hydrophobic molecule (e.g., PEG) is added to the crude solution;
3. the top PEG phase, containing cell debris, proteins and reactive nitrogen-containing compounds, is discarded;
4. more PEG is then added to the bottom salt phase containing the target protein;
5. the top PEG phase, containing proteins and reactive nitrogen-containing compounds (e.g., ammonia), is discarded;
6. the bottom salt phase, containing the target protein, is then optionally run through Step 4 again, or has added thereto, more PEG and the PEG-chelator-metal complex;
7. the bottom salt-containing phase is discarded;
8. the top PEG phase, containing the target protein bound to the PEG-chelator-metal complex has then added thereto a salt, thereby producing a two-phase system. Following an appropriate method for disrupting the complex, e.g., by pH adjustment, addition of a competitive inhibitor or strong chelator, the top phase contains PEG and ligand and the bottom, salt phase, contains the target protein. The target protein may be pure at this point, or may be subject to further purification or polishing.

The instant invention also relates to novel metal chelating compounds. More specifically, the novel metal chelating compounds include poly (ethylene glycol) methyl ether ("MPEG")-diethyltriamine ("MPEG-DETA").

There are also provided novel methods for synthesizing MPEG-DETA and novel intermediate compounds used in the synthesis thereof.

Also provided are methods for selectively enhancing the solubility of a target protein.

More particularly, the target protein is reversibly bound with a polymer-chelator-metal complex, e.g., Cu(II)IDA-PEG, to enhance its solubility in an aqueous solution comprising a hydrophobic polymer, preferably the same as that used in the polymer-chelator-metal complex.

DETAILED DESCRIPTION OF THE INVENTION

As used herein, "PEG-chelator-metal complex" refers to all such complexes useful in the instant invention. Although "PEG" is often used, it is meant to be shorthand, and should be understood as including all inert hydrophobic molecules that are useful in such a complex, some of which are described below. "Polymer" is also used similarly, e.g., polymer-chelator-metal complex. Various chelators and metals useful in the "PEG-chelator-metal complex" are described below.

Although the preferred time for adding the PEG-chelator-metal complex is set forth above, it may be added at various other times during the process, including after some preliminary purification or clarification steps, although there will be at least some non-target proteins present in the solution.

Proteins suitable for purification according to the methods of the instant invention ("target protein(s)") include proteins that can bind with sufficient selectivity to the PEG-chelator-metal complex. Such proteins include proteins that contain surface active amino acids that can act as electron donors. These amino acids include for example lysine, arginine, histidine, cysteine, glutamic acid, and aspartic acid. Proteins with a high number of histidine or cysteine residues on their surfaces are particularly well suited for purification according to the methods of the instant invention. The histidines or cysteines may be naturally occurring histidines, as in the case of, for example, myoglobin and hemoglobin, or they may be amino acids that have been added to the protein through genetic engineering techniques (Vosters, A. F., D. B. Evans, W. G. Tarpley and S. K. Sharma (1992) Protein Expr. and Purif. 3: 18–26; Lilius, G., M. Persson, L. Bülow and K. Mosbach (1991) Eur. J. Biochem. 198: 499–505; Ljungquist, C., A. Breitholts, H. Brink-Nilsson, T. Moks, M Uhlén and B. Nilsson (1989) Eur. J. Biochem. 186: 563–569).

The crude or partially purified protein solution containing the target protein according to the methods of the instant invention can be obtained from any source. For example, some procaryotic or eucaryotic cells may naturally produce the protein of interest. For example, if the protein of interest is native hemoglobin, hemoglobin-containing cells suitable as starting material for the present invention are readily available from a number of sources. Such sources include, but are not limited to, outdated human red blood cells, bovine red blood cells and a number of non-red blood cell sources including, but not limited to, bacterial, yeast, plant, and mammalian cells as set forth below. Also, transgenic animals may be produced that can express the target protein, including mutant, non-mutant or transgenic hemoglobin, red blood cells and their progenitors.

In addition to naturally occurring expression of the target protein in naturally occurring eucaryotic or procaryotic systems, recombinant systems can be created that produce the target protein. The genes encoding the target protein can be placed in a suitable expression vector and inserted into a microorganism, animal, plant, insect or other organism, or inserted into cultured animal or plant cells or tissues. These organisms, cells or tissues may be produced using standard recombinant DNA techniques and may be grown in cell culture or in fermentations. For example, human alpha and beta globin genes have been cloned and sequenced by Liebhaber et al. (Proc. Natl. Acad. Sci. USA 77: 7054–7058, 1980) and Marotta et al. (J. Biol. Chem. 252: 5040–5053, 1977) respectively. Techniques for expression of both native and mutant alpha and beta globins and their assembly into hemoglobin are set forth in U.S. Pat. No. 5,028,588 to S. J. Hoffman, incorporated herein by reference; K. Nagai and Hoffman, S. J. et al., PCT/US90/02654; Townes, T. M. and McCune, S. L., PCT/US91/09624; and De Angelo, J. et al., PCT/US91/02568 and PCT/US91/08108.

After the protein has been expressed in the desired system to the desired level, it generally should be released from the cell to create a crude protein solution. This can usually be accomplished by breaking open the cells, e.g., by sonication, homogenization, enzymatic lysis or any other cell breakage technique known in the art. The proteins can also be released from cells by dilution at a controlled rate with a hypotonic buffer so that some contamination with cellular components can be avoided (Shorr et al., U.S. Pat. No. 5,264,555). In addition, cells may be engineered to secrete the protein of interest by methods known in the art.

After breakage of the cells, or secretion, the target protein is contained in a crude cell lysate or a crude cell broth or solution. The protein may be purified according to the methods of the invention at this stage, or may be clarified by removal of the solid debris to form a clarified cell lysate or clarified cell broth. However, there is no need to clarify the lysate to purify the protein according to the methods of the instant invention.

The crude or clarified target protein-containing solutions also can be extracted with a non-metal affinity two-phase aqueous system comprising hydrophobic molecule and salt. Preferably, the hydrophobic molecule is the same as the hydrophobic polymer used in the polymer-chelator-metal complex used subsequently. This extraction can be done prior to purification with the two-phase metal affinity aqueous system of the instant invention. To reduce the total load of contaminating protein, precipitation can be used prior to extraction. Precipitation may offer some processing advantages if it does not also result in target protein precipitation. Following extraction, the target protein can be separated from the polymer by tangential flow filtration or any other conventional method of dialysis. Suitable salts include, for example, sodium sulfate, potassium phosphate, ammonium sulfate and magnesium sulfate. Magnesium sulfate is preferred. The salt is preferably added to the crude or clarified protein solution prior to the addition of the inert hydrophobic molecule to avoid precipitation of the target protein. Phase separation can be achieved by any suitable method, such as, for example, centrifugation or equilibration and sedimentation.

Suitable inert hydrophobic molecules include any such molecules that are more hydrophobic than the salt phase of the two-phase system, that are still highly water soluble. Such molecules include poly(alkaline oxide)s such as polypropylene oxide and PEG. PEG molecules, for example, can be from molecular weight of approximately 400 to 20,000. Particularly suitable molecular weights of PEG are 1000–8000.

The partitioning of the cell debris can be directed to either phase of the two-phase aqueous system. This can be accomplished by adjusting the density of the salt phase so that it exceeds the average density of the sedimenting cellular debris. The aqueous two-phase system can also be used to complete clarification of cell lysate following coarse solids removal by any method known in the art, such as filtration or centrifugation. Using the methods of the instant invention, unsedimented cell debris consistently partitions to the liquid-liquid interface yielding a well-clarified protein-rich salt phase.

The partitioning step using the inert hydrophobic molecule and salt may be repeated more than once. It is particularly useful as a method for removing contaminating proteins and ligand-binding inhibitors such as reactive nitrogen-containing compounds, e.g., ammonia, that can inhibit subsequent metal-chelator binding, from the crude solution. The target protein at this stage will be found in the salt portion of the hydrophobic molecule/salt two-phase aqueous system.

The PEG-chelator complex is then charged with a transition metal ion. Suitable transition metal ions include iron, nickel, zinc, cobalt and copper.

Next, the polymer-metal-chelator complex is added to the salt solution together with more of an inert hydrophobic molecule, preferably PEG if PEG is the hydrophobic polymer used in the complex.

Suitable metal chelating molecules include any chelators that are known in the art for metal affinity chromatography. Such chelators include N,N,N'-tris(carboxymethyl) ethylenediamine (TED) (Hochuli, E., H. Döbeli, and A. Schacher, J. Chroma., 411: 177–184 (1987)) iminodiacetic acid (IDA) and diethylene triamine (DETA), which is used to produce a novel polymer-chelator compound as taught herein.

The metal chelators can be conjugated to the inert hydrophobic molecules using any suitable method in the art. A suitable technique for the formation of the PEG-metal chelator conjugate is by formation of the chloride derivative of a methoxy-PEG molecule followed by reaction of the methoxy PEG chloride derivative with the soluble metal chelator. The novel synthetic methods to produce PEG-DETA are set forth herein.

After the protein of interest is concentrated in the PEG-rich phase, it can be further extracted to a fresh salt phase by disassociation of the metal chelator-protein complex. Otherwise, the PEG phase can be processed with further extraction by tangential flow filtration or chromatography. The inert hydrophobic molecule-chelator-metal complex can be removed from the purified target protein by subsequent extraction with a further two-phase aqueous salt/inert hydrophobic molecule system that does not contain the metal chelator.

If there are high concentrations of inhibitors of metal chelate binding present in the crude or clarified protein solution, such inhibitors should be removed prior to metal affinity partitioning. Inhibitors of metal chelate binding include imidazole, and especially ammonium. Removal of these inhibitors can be accomplished by any means known in the art, for example by sparging at high pH or by successive back extraction of the protein rich salt phase as set forth above. Alternatively, the amount of inhibitor present in the crude or clarified lysate may be reduced by adding less of such inhibitors, such as ammonium hydroxide, during, for example, fermentation processes.

Dissociation of the protein-metal-chelate complex (e.g., the recombinant hemoglobin Cu(II)IDA-PEG complex set forth herein) can be accomplished by lowering the pH, addition of a competing electron-donor such as imidazole or $NH_4Cl$, or by addition of a strong chelator such as EDTA. The latter approach is preferable in particular when heme proteins are the target proteins because complete chelation of copper is desirable to prevent oxidation of the protein. Following dissociation, the PEG-phase containing the protein of interest can be applied directly to a chromatographic polishing step or first extracted back into a salt-rich phase prior to chromatography, depending on the separation mechanism (ion exchange, size exclusion, etc.). Using either approach, PEG and metal chelate can be recovered and reused.

The successful application of metal affinity partitioning as a protein isolation method when copper is used requires an effective strategy to minimize copper-catalyzed oxidative damage. Three mitigation strategies are part of the instant invention: formation of HbCO, reduced temperature, and the use of a stronger chelate. Each has individually led to reduced methemoglobin formation. By combining the first two strategies it has been possible to partition hemoglobin with minimal heme oxidation in the presence of Cu(II)IDA-PEG.

Heme oxidation could also be prevented by the use of Zn(II) or Ni(II) coupled to IDA since these transition metal ions are not redox reactive. However, these metal ions form a weaker complex with IDA and their use has led to hemoglobin precipitation. However, with the stronger metal chelates of the invention, such as MPEG-DETA, Zn(II) can be used for metal affinity hemoglobin partitioning.

Some hemoglobin oxidation occurs during metal affinity partitioning of native human hemoglobin with Cu(II)IDA-PEG. Oxyhemoglobin undergoes rapid oxidation by Cu(II) IDA-PEG while the rate of heme oxidation for carbonmonoxyhemoglobin is greatly reduced. The rate of heme oxidation is reduced for Cu(II)-DETA compared with Cu(II) IDA, both of which are tridentate chelates.

According to the methods of the instant invention, partitioning at low temperature also can reduce the rate of MCO reactions that can occur at the heme and to amino acid side chains on the protein. The rate of heme oxidation is reduced at 4° C. at a Cu(II)IDA-PEG/hemoglobin ratio of 50.

EXAMPLE 1

Preparation of *E. coli* Cell Lysate Containing Mutant Hemoglobin

*E. coli* were grown and fermented as described in PCT publication number WO 95/14038, incorporated herein by reference. *E. coli* strain 1662, described in PCT publication number WO 95/14038, was used in the fermentation. The cells were lysed as described in PCT WO 95/14038 using Niro cell disruptor (Niro Hudson, Inc., Hudson, Wis.). The resulting crude lysate containing mutant hemoglobin rHb1.1 was used without further modification or processing.

EXAMPLE 2

Preparation of Aqueous Two-phase Systems

Aqueous two-phase systems were prepared by fully dissolving $MgSO_4.7H_2O$ in the cell lysate from Example 1 followed by addition of stock 50% (w/w) PEG 1000 solutions to obtain the desired final system composition, and equilibrating for 30 minutes at 4° C.

Reversing the order of addition in some cases resulted in mutant hemoglobin precipitation. Phase separation was typically accomplished by centrifugation at 2000 rpm for 5 minutes using a refrigerated JA-14 rotor (Beckman Instruments, Fullerton, Calif.) at 4° C. Samples were prepared by dilution of small aliquots in 50 mM HEPES.

EXAMPLE 3

Effect of PEG Molecular Weight on *E. coli* Protein Partitioning

The ability to manipulate the PEG-phase partitioning of certain *E. coli* proteins in the absence of a metal chelate was demonstrated by varying the PEG molecular weight in an aqueous two-phase system. A series of 8.8 gram systems was prepared at 4° C. containing 18% (w/w) PEG and 9% (w/w) $MgSO_4$ in partially clarified cell lysate containing recombinant mutant hemoglobin (rHb1.1, described in, for example, PCT publication WO 90/13645, incorporated herein by reference). These systems were prepared by centrifugation at 5000 rpm for 30 min., JA-14 rotor). Stock solutions of PEG 400 and PEG 1000 (50 wt %) were added to each system to obtain a weight average PEG molecular weight of 400, 600, 800, and 1000. Only the systems containing 800 and 1000 molecular weight PEG formed two-phase systems, having phase volume ratios of 6.8 and 1.7, respectively. The top-phase protein composition for the PEG 1000 system was analyzed by SDS-PAGE. A large number of native *E. coli* proteins partitioned to the PEG-rich phase while recombinant hemoglobin remained exclusively in the lower salt-rich phase.

The UV-visible absorbance of each phase confirmed the partitioning of recombinant hemoglobin to the salt phase and a significant portion of the native *E. coli* protein to the PEG-rich phase. A second back extraction of the salt-phase with PEG 1000 showed additional but diminished extraction of native *E. coli* proteins to the PEG-rich phase.

In addition, high MW proteins (MW>~50 kDa) tended to favor the salt-rich phase. Proteins were increasingly excluded from the PEG-rich phase when either the protein or polymer MW increased. For example, PEG-phase protein partitioning of *E. coli* proteins was greatly reduced when PEG 8000 was used as the phase forming polymer. Thus, contaminating protein can be removed by adjustments of the polymer molecular weight prior to metal affinity partitioning of the target protein.

EXAMPLE 4

Partitioning of Cell Debris

An aqueous two-phase system (10 gram total weight) was prepared in fresh unclarified *E. coli* cell homogenate containing rHb1.1 composed of 5% PEG1000 (w/w) and 18% $MgSO_4$ (w/w) at 4° C. Following centrifugal separation (5000 rpm, 5 min., JA-14 rotor), the cell debris partitioned entirely to the top phase, forming a viscous, gelatinous top-phase. Operation along the same tie-line at a higher phase volume ratio can be used to accommodate the cell debris while leaving the phase densities unchanged. Using the methods of the it invention it is possible to define a region of the phase diagram in which bottom-phase or top-phase cell debris sedimentation occurs to suit particular application needs.

EXAMPLE 5

Production of PEG-metal Chelator Complex

IDA-PEG 750 and IDA-PEG 5000 were prepared from methoxy-PEG 5000 (MPEG 5000) and methoxy-PEG 750

(MPEG 750) (CARBOWAX, Sigma Chemical Company, St. Louis, Mo.) by minor modifications (described below) to published methods (Chung, B. H., Bailey, D., and Arnold, F. H. 1994. In: Methods in Enzymology, Vol. 228, H. Walters, and G. Johansson (eds), pp. 167–179)

Synthesis of Cu(II)IDA-MPEG

MPEG-IDA 750 was prepared first. Note that the number refers to the molecular weight of the MPEG molecule conjugated to the metal chelator. The synthesis was monitored by Fourier Transform Infrared spectroscopy (FTIR) using a Nicolet FTIR (Nicolet Instruments, Madison, Wis.). The synthetic approach was then applied to the synthesis of MPEG-IDA 5000 (see below). Size exclusion chromatography was performed on a Beckman high performance liquid chromatograph ("HPLC") (Beckman Instruments, Inc., Fullerton, Calif.) using a TSK G3000PWx1 column (7.5 cm×30 cm, TosoHaas, Montgomeryville, Pa.). Ion exchange chromatography was performed using a TSK DEAE 5PW column (7.5cm×15 cm, Beckman Instruments, Fullerton, Calif.). All polymer concentrations were determined using a Waters Model 401 refractive index detector (Millipore, Waters Chromatography Division, Milford, Mass.).

Preparation of MPEG-Cl 750 and MPEG-Cl 5000

MPEG 750 (25.68 g, 34.24 mmoles) was dried by distillation from toluene in vacuo. Following addition of 95 ml (1.302 moles) of freshly distilled thionyl chloride the reaction was refluxed for 9 hr. under nitrogen. Excess thionyl chloride was removed by vacuum distillation. The yellow residue was dissolved in 50 ml of chloroform, filtered, and precipitated with 500 ml of ethyl ether at $-20°$ C. or $4°$ C. for MPEG-Cl 5000. The product was recrystallized twice from chloroform/ethyl ether and dried under vacuum; yield 12.72 g. (48.3%), (97.4% yield from MPEG-5000); i.r. (neat) 663 $cm^{-1}$ (C-Cl), no absorption for OH at 3473 $cm^{-1}$. Size exclusion chromatography of MPEG-Cl 5000 (1.5 ml/min., 0.05M potassium phosphate) showed no change in molecular weight relative to the starting material.

Preparation of MPEG-IDA 750 and MPEG-IDA 5000

MPEG-IDA 750 was prepared by reaction of MPEG-Cl 750 (1.00 g, 1.301 mmoles) with IDA (0.868 g, 6.52 mmoles) and potassium carbonate (2.70 g, 19.53 mmoles) in 35 ml of water for 24 hours at reflux (90°–95° C.). The reaction mixture was adjusted to pH 3.0 with concentrated HCl and extracted with 100 ml of 40/60 (v/v) chloroform/ethanol. The extract was concentrated, dried with anhydrous $K_2CO_3$, filtered, and precipitated with ethyl ether at $-20°$ C. ($4°$ C. for MPEG-IDA 5000). The product was recrystallized twice from 40/60 chloroform/ethanol and ether and dried under vacuum; yield 0.39 g. (34.5%), (80.2% yield from MPEG-Cl 5000); i.r. (neat) 1729 $cm^{-1}$, 1640 $cm^{-1}$ (CO), no absorption for CCl at 663 $cm^{-1}$. Ion exchange chromatography of the MPEG-IDA 5000 (0.5 mi/min., 0.01M Tris, pH 8) showed 81% reaction completion.

Preparation of Cu(II)IDA-PEG 5000

Cu(II)IDA-MPEG was prepared by charging $Cu(II)SO_4$ (6.24g, 39.10 mmoles) to a 100 ml solution containing MPEG-IDA 5000 (20.0 g, 3.91 mmoles) in 0.2M sodium acetate, pH 4.0. The solution was equilibrated for one hour, extracted twice with 60/40 (v/v) chloroform/ethanol, precipitated with ethyl ether and dried. Approximately 5 gms of the product was dissolved in 50 ml deionized water, filtered, and dialyzed for 24 hours with deionized water in a continuous-flow Nucleopore stircell equipped with a 3000 MW cut off membrane and wash reservoir. The product was dried and a yield of 86.0% was obtained. The copper content was analyzed by inductively coupled plasma ("ICP") atomic absorption to be 82.1%, or 99% of the product chelated with Cu(II).

EXAMPLE 6

Metal Affinity Partitioning of Recombinant Hemoglobin

Recombinant hemoglobin, produced according to Example 1, was successfully partitioned into the PEG-rich phase from clarified cell lysate with Cu(II)IDA-PEG. An aqueous two-phase system (8.8 g. total weight) containing 18% (w/w) PEG 1000 and 9% (w/w) $MgSO_4$ was prepared in partially clarified E. coli cell lysate (5000 rpm, 5 min., JA-14 rotor) at $4°$ C. The top phase was carefully removed and the salt-rich phase (containing rHb1.1) was back-extracted with fresh PEG 1000 prepared in chilled 50 mM HEPES, pH 7.5 at $4°$ C. Chilled PEG 1000 in 50 mM HEPES $4°$ C., pH 7.5, was again added to form a two-phase system of approximately the original composition. Cu(II)IDA-PEG (9.6% w/w) was then added in increasing molar excess of 24.5, 73.5, and 147.1 and the top phase extract analyzed by SDS-PAGE and UV-visible absorption. SDS-PAGE analysis was performed using 8–25% gradient gels on a PhastGel (Pharmacia) electrophoresis unit followed by silver staining. Molecular weight standards (See Blue™) were obtained from Novex (San Diego, Calif.) pre-stained standards: myosin 250 kDa; BSA, 98 kDa; glutamic dehydrogenase, 64 kDa; alcohol dehydrogenase, 50 kDa; carbonic anhydrase, 36 kDa; myoglobin, 30 kDa; lysozyme, 16 kDa; aprotinin, 6 kDa; and insulin, B chain, 4 kDa). UV-visible spectroscopy was performed on an HP 8542 diode array spectrophotometer. Hemoglobin concentrations were measured at 410 nm $\epsilon=1.25\times10^5$ $M^{-1}$ $heme^{-1}$.

Increasing ligand loading resulted in an increase in rHb1.1 partitioning. The ligand was selective for the hemoglobin. At the highest loading tested, complete PEG-phase partitioning of hemoglobin was observed as monitored by the disappearance of the Soret absorption at 410 nm in the salt-phase.

EXAMPLE 7

Effect of Ammonia Inhibition on Protein Partitioning

Ammonia, which can be present in fermentation broths in concentrations in excess of 0.3 M (as $NH_3/NH_{4+}$), is known to be an effective inhibitor of metal chelate binding and is often used to elute proteins during immobilized metal affinity chromatography. Removal of ammonia is therefore helpful for successful metal affinity partitioning of proteins from crude cell lysate. Repeated extraction of cell lysate with fresh PEG solution was tested as a method of reducing ammonia prior to metal affinity partitioning. Four 9 gram aqueous two-phase systems containing 15% (w/w) PEG 8000 and 6.5% (w/w) $MgSO_4$ were prepared from partially clarified cell lysate at $4°$ C. The top-phase from three of these systems was carefully decanted and the rHb1.1-rich salt-phase back-extracted with fresh chilled PEG 8000 to the same original system composition at pH 8.0. Back-extraction was repeated to ultimately produce four systems containing a decreasing concentration of ammonia. The pH of each system was finally adjusted to 7.3 at 4° C. Cu(II) IDA-PEG was then added to each system and the rHb1.1 partition coefficient measured. Protein partition coefficients increased with each successive back extraction as inhibitory ammonia was removed. Following three back extractions, the measured partition coefficients were still below the predicted values, indicating that ligand inhibition remained.

However, back extraction was successful in removing some inhibiting ammonia. After three successive back extractions, the crude lysate was subjected to extraction with the two-phase metal affinity partitioning. Again the ability of Cu(II)IDA-PEG system of the instant invention to recognize and selectively partition rHb1.1 from crude lysate was confirmed compared with the distribution of unpartitioned proteins in the bottom salt-phase.

EXAMPLE 8

Prevention of Oxidation of Hb by Cu(II)IDA-PEG

Metal-catalyzed oxidation reactions are ubiquitous degradation processes which often result in irreversible protein damage including the covalent modification of labile amino acid residues (Stadtman, E. R., Berlett, B. S. 1991. Fenton Chemistry: Amino Acid Oxidation. J. Biol. Chem. 266:17201–17211) and the oxidation of metal-containing prosthetic groups (Rifkind, J. M,. 1974. Copper and the autoxidation of hemoglobin, Biochemistry, 13, 2475). Copper is among the most redox-reactive transition metal ions, and great care must be taken in the use of metal-affinity protein isolation techniques which use chelated copper as the metal ligand. For example, MCO reactions have been implicated in IMAC using Cu(II)IDA. Krishnamurthy, R., Madurawe, R. D., Bush, K. D., and Lumpkin, J. A. 1995. Conditions promoting metal-catalyzed oxidations during immobilized Cu-iminodiacetic acid metal affinity chromatography. Biotechnol. Prog. 11:643–650.

This example sets forth methods to mitigate MCO reactions during metal-affinity partitioning.

Materials

Cu(II)IDA-PEG was prepared following the method described in Example 5 and exhaustively dialyzed to remove traces of unchelated metal ion. Atomic absorption ICP analysis of the polymer-metal-chelate showed a 99% chelation efficiency. $CuSO_4$ was obtained from Aldrich (Milwaukee). The chelones, IDA, EDTA, and DETA were obtained from Sigma (St. Louis).

Preparation of $HbO_2$ and HbCO

Oxyhemoglobin ($HbO_2$) was prepared from whole blood as follows:

Fresh human hemoglobin was collected and centrifuged at 4° C. for 10 minutes at 650 g to separate the erythrocytes using a Sorval SS-H6 rotor. The cells were lysed by addition of chilled 0.9% (w/w) NaCl (pH7 and purged with carbon monoxide) to twice the original volume and centrifuged at 4° C. for 60 minutes at 24,000 g. The supernate was decanted and the procedure repeated two more times. The crude hemolysate was suspended to the original volume in 0.050 M Tris buffer, pH 8.0, containing 0.001 M EDTA previously purged with carbon monoxide, and dialyzed in 12,000 MW cut off Spectrapor dialysis tubing for 40 hours against 5 liters of the same buffer. After dialysis, the lysed erythrocytes were centrifuged at 4° C. for 60 minutes at 24,000 g and the supernate carefully pipetted and filtered through a double layer of polyester silk screening cloth to remove unsedimented stroma. The pellet and thicker hemolysate near the bottom of the centrifuge tube was discarded. Tris buffer was added to the filtered supernate to the original volume and the centrifugation and screening steps were repeated. The hemolysate was loaded onto a 5×50 cm column containing 100 g of DEAE-Sepharose A50 and eluted with 0.050M Tris/0.001 M EDTA, pH 7.90. Two main fractions were collected and pooled. Aliquots of purified hemoglobin were concentrated to 50–100 g/L when needed by transferring 15 ml from the pooled fraction to Centricon 30 concentrators (Amicon) and centrifuging at 4° C. for 30 minutes at 2000 g. The retentate was diluted to 15 ml with the desired buffer and then centrifuged at 4° C. for 30 minutes at 2000 g and repeated two more times. The hemoglobin solution was finally concentrated to a final volume of about 1–2 ml.

Carbonmonoxy hemoglobin (HbCO) was prepared by sparging the headspace with CO while stirring for 30 minutes in a glass vial fitted with a septum. After sparging, a pressure of 20 psig was left on the sample. Conversion to HbCO was confirmed by the shifting of the absorbance maxima from 542 nm and 576 nm for $HbO_2$ to 540 nm and 570 nm for HbCO. When required, HbCO was converted back to $HbO_2$ by purging the sample headspace for 60 minutes with humidified oxygen with vigorous stirring at 4° C.

Absorbance Measurements

Absorbance measurements of protein solutions were made using a Hewlett-Packard HP5842 diode array spectrophotometer. Samples containing Cu(II) and oxyhemoglobin were prepared in one of two ways. For the ambient temperature oxidation experiments, the cuvette containing the reaction mixture was placed in the spectrophotometer and analyzed at discrete time intervals. For the low temperature oxidation experiments, a sample aliquot was quenched by dilution in buffer solution containing 1 mM EDTA and analyzed at ambient temperature. For measurements of the oxidation of HbCO by Cu(II), the spectrophotometer was equipped with a 80 μl flowcell and sipper pump downstream of the flowcell and sample reservoir.

Copper-catalyzed Oxidation of Oxyhemoglobin

Formation of methemoglobin resulting from the oxidation of the heme iron by unchelated copper is noted by an increase in absorbance maxima at 500 nm and 630 nm and a corresponding decrease in absorbance maxima at 542 nm and 576 nm for reduced oxyhemoglobin. Initial oxidation occurs rapidly as Cu(II) is reduced by the heme iron to Cu(I). Heme oxidation continues at a much slower rate as Cu(I) is re-oxidized by $O_2$ to Cu(II), completing the catalytic cycle. (Rifkind, JM 1974. Copper and the autoxidation of hemoglobin. Biochem. 13:2475–2481) Oxidation is initiated by the binding of Cu(II) to a high-affinity copper binding site followed by the dissociation of oxygen from the sixth ligand position of the heme and is completely prevented by the addition of a strong chelator such as EDTA.

The effectiveness of a chelator depends of the magnitude of the metal-ion stability constant relative to the intrinsic association constant of the binding site. While the tridentate chelator IDA affords some protective effect, heme oxidation occurs at only a slightly reduced rate. Thus, the intrinsic association constant for the metal binding site must be similar to the Cu(II)IDA stability constant (log K=10.63). Martell, A. E. and Smith JM 1975. Critical Stability Constants. Vol 2 Amines. Plenum Press, New York.

Copper chelation by IDA appears to minimize the formation of protein precipitates in comparison with non-chelated copper. Non-chelated copper and zinc were observed to cause rapid precipitation of hemoglobin, as measured by an increase in general light scattering. On the other hand, no precipitation was observed for chelated copper up to a loading of at least 43.5 molar equivalents.

If hemoglobin is capable of effectively competing with IDA for copper, then heme oxidation can be further minimized by the use of a stronger tridentate chelator such as bis-imino(2-ethlyamine), also called diethylenetriamine (DETA), the structure of which is shown below.

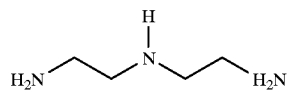

Diethylenetriamine (DETA)

The stability constant for equal molar Cu(II)-DETA is very large (log K=15.9). Martell, A. E. Smith, R. M. 1975. Critical Stability Constants. Vol. 2 Amines, pp.101. Plenum Press, New York. Therefore, the rate of hemoglobin oxidation was measured for equal molar amounts of Cu(II) chelated with EDTA, DETA, and IDA and compared with unchelated copper. The tridentate chelone DETA is nearly as effective as EDTA (log K=18.7) at preventing heme oxidation. At 10 molar equivalents of DETA, complete protection was observed while a 1000 molar excess of IDA was required to achieve the same level of protection. In the presence of equal molar amounts of DETA and Cu(II), heme oxidation is only slightly increased with increased copper loading.

Copper-catalyzed Oxidation of Carbonmonoxy Hemoglobin

HbCO oxidation experiments were conducted using a flowcell to completely exclude air from the solution. Following injection of a small aliquot of Cu(II)IDA-PEG, previously purged with CO, to a screw-cap vial containing HbCO, the sample was pumped through the flowcell and the absorbance measured over time. A uniform increase in absorbance was observed but the isobestic absorbances vanished, suggesting some precipitation but no heme oxidation. If a correction is made for increased light scattering, HbCO proves to be stable under conditions of high copper loading. Under similar conditions the addition of excess Cu(II)SO$_4$ caused rapid protein precipitation but no measurable heme oxidation.

Copper-catalyzed Oxidation of Oxyhemoglobin at Reduced Temperature

Since the rate of a chemical reaction depends on temperature, the effect of temperature on copper-catalyzed heme oxidation was investigated. Lowering the reaction temperature to 4° C. from 20° C. increased the stability of oxyhemoglobin toward heme oxidation by Cu(II).

EXAMPLE 9

Solubility of Hb in PEG-salt Aqueous Two-phase Systems: Choice of Salt System

Plunkett and Arnold reported that precipitation at the interface of aqueous two-phase systems accounted for 25% of the total hemoglobin added during metal affinity partitioning in a system of PEG 5000 and sodium sulfate. Low protein solubility has frequently been noted in the aqueous two-phase partitioning literature. Kohler (Kohler, K., Veide, A., Enfors, S.-O.1991. Enzyme Microb. Technol. 13: 204–209) observed that the partitioning of β-galactosidase and β-galactosidase fusion proteins was hampered by the low solubility of β-galactosidase in potassium phosphate at concentrations (11–13%) typical in the heavy phase. Asenjo et al. (Asenjo, J. A., Schmidt, A. S., Hachem, F., Andrews, B. A. 1994. J. Chrom. A. 668: 47–5) observed low solubility of α-amylase in potassium phosphate and sought to derive an apparent partition coefficient to account for the accumulation of interfacial protein precipitates. Similar results have also been observed for metal affinity partitioning of hemoglobin and myoglobin in aqueous two-phase systems composed of sodium sulfate or potassium phosphate. (Wuenschell, et al., 1990 Bioprocess Engr. 5:199–202)

Therefore, the solubility of hemoglobin in a variety of phase-forming salts was investigated. The solubility of hemoglobin was compared at the salt concentration range of the bottom phase for aqueous two-phase systems formed by potassium phosphate, sodium sulfate, and magnesium sulfate. The solubility of hemoglobin is less then 1.0 mg/ml for the two-phase systems composed of sodium sulfate and potassium phosphate. The solubility of hemoglobin in MgSO$_4$ is in the range of 20–30 g/L.

The solubility of hemoglobin increases with decreasing temperature under salting-out conditions. Experiments conducted indicated that the solubility of human hemoglobin at 4° C. is at least 50 g/L in 1M to 2 M MgSO4. Wile not wishing to be bound by theory, the high solubility of hemoglobin in MgSO4 may be due to binding of Mg$^{2+}$ to the protein, preventing hydrophobic interactions that can lead to protein salting-out. Magnesium binding to negatively charged acid residues has been implicated in the extreme sat-phase partitioning of recombinant Vitreoscilla hemoglobin during aqueous two-phase partitioning in PEG-magnesium sulfate. Hart R. A. and Bailey, J. E. 1991. Enzyme Microb. Technol. 13:24–30) With the use of MgSO$_4$ as the phase-forming salt, no interfacial precipitation was observed during metal affinity partitioning. The choice of salt plays a key role in the use of aqueous two-phase protein extraction from crude lysate. The other salts commonly used (Na$_2$SO$_4$, KHPO$_4$) result in protein precipitation due to salting out at the centrification typical in aqueous two-phase systems. Furthermore, these salts cannot be used at low temperature due to their limited solubility. MgSO$_4$ is a preferred salt due to its apparent "salting-in" ability and high solubility at low temperature, making it suitable for partitioning redox sensitive proteins at moderate concentration.

EXAMPLE 10

Synthesis of a Novel Metal Chelating Compound MPEG-DETA

This example sets forth the synthesis is of a new metal affinity ligand, MPEG-DETA, useful in the application of metal affinity isolation techniques to redox labile proteins.

Poly(ethylene glycol) methyl ether ("MPEG") was obtained from Aldrich (Milwaukee) in 750 and 5000 average molecular weights. All other reagents were obtained from Aldrich.

MPEG-DETA was synthesized according to the five-step sequence of reactions shown in Chart A. MPEG 750 was used as the starting material and structural analysis of each reaction step was conducted using Perkin-Elmer and Nicolet Fourier Transform Infrared (FTIR) Spectrophotometers.

Preparation of MPEG-Cl (Step 1, Chart A)

MPEG-Cl was prepared by chlorination of MPEG 750 with thionyl chloride following the procedure of Bayer, et al. Bayer, E., Zheng, H., and Geckeler, K. 1982. Functionalization of soluble polymers 4. Synthesis of dichloro- and di(4-formylphenyloxyethyl) poly(oxyethylene). Poly. Bull. 8:585–592. In a typical reaction, 35 g of MPEG 750 (34.4 mmoles) was dried by azeotropic distillation from toluene in vacuo. Following addition of 95 mL (1.3 moles) of freshly distilled thionyl chloride the reaction was refluxed for 9 hours under a nitrogen atmosphere. Excess thionyl chloride was then removed by vacuum distillation. The yellow residue was dissolved in 50 mL of chloroform, vacuum filtered, and precipitated with 500 mL of diethyl ether at −20° C. The product was recrystallized twice from chloroform/diethyl ether (1:10, v:v) and dried under vacuum to yield 12.72 g. (48.3% yield) of MPEG-Cl (MW 768.45). FTIR results indicate complete conversion to the monochloride: (neat) 663 cm$^{-1}$ (C-Cl), no absorption for OH at 3473 cm$^{-1}$.

Preparation of MPEG-DEA (Step 2, Chart A)

MPEG-Diethanolamine (MPEG-DEA) was prepared from MPEG-Cl 750 by reaction with Diethanolamine (DEA) in water. To 3.98 g of MPEG-Cl (5.18 mmoles) dissolved in 70 mL of water was added 3.58 g $K_2CO_3$ (25.0 mmoles) and 2.73 g of DEA (25.96 mmoles). The mixture was refluxed for 24 hours. After cooling, 17.5 g of $Na_2SO_4$ were added to form two phases and the upper polymer phase containing the product was collected. The upper phase was extracted once with 100 mL of chloroform/ethanol (1:1.5, v:v), dried over anhydrous $MgSO_4$ and concentrated by distillation of the solvent. The solid residue was dissolved in 10 mL of chloroform and precipitated with 100 mL of diethyl ether at −20° C. The product was dried under vacuum to yield 2.69 g (62% yield) of MPEG-DEA (MW 837.14). FTIR results indicate nearly complete conversion to the product: (neat) 3468 cm$^{-1}$ (OH), disappearance of C-Cl absorbance at 663 cm$^{-1}$.

Preparation of MPEG-DECA (Step 3, Chart A)

MPEG-DEA was converted to the bis-chlorinated product MPEG-diethylchloroamine (MPEG-DECA) with thionyl chloride following the procedure of Bayer, et al. In a typical reaction, 2 g of MPEG-DEA (2.39 mmoles) was dried by azeotropic distillation from toluene in vacuo. Following addition of 16 mL (219.4 mmoles) of freshly distilled thionyl chloride, the reaction was refluxed for 9 hours under a nitrogen atmosphere. Excess thionyl chloride was removed by vacuum distillation. The yellow residue was dissolved in 20 mL of chloroform, vacuum filtered, and precipitated with 200 mL of diethyl ether at −20° C. The product was recrystallized twice from chloroform/diethyl ether (1:10, v:v) and dried under vacuum to yield 1.44 g. (70.0%) of MPEG-Cl (MW 874.05). FTIR results indicate complete conversion to the bis-chloride: (neat) 663 cm$^{-1}$ (C-Cl), no absorption for OH at 3473 cm$^{-1}$.

Preparation of MPEG-DAEA (Step 4, Chart A)

MPEG-DECA was converted to the diazido product, MPEG-diazidoethylamine (MPEG-DAEA) by reaction with sodium azide following the procedure of Zalipski (Zalipski, E. 1983. Eur. Polym. J. 19:1177). A solution of 0.5 g of MPEG-DECA (0.58 mmoles) in 2.8 g of DMF was prepared followed by the addition of 0.66 g of sodium azide (10.2 mmoles) in one portion. The solution was heated for 2 hrs at 120–130° C. The excess sodium azide was filtered and the solvent removed by distillation in vacuo. Dichloromethane was added and the product precipitated by addition of diethyl ether (1:10) chilled to −20° C. The precipitated product was recrystallized once from dichloromethane/diethyl ether (1:10, v:v). The yield was approximately 0.2 g. FTIR results indicate complete conversion to the azide: (neat) 2100 cm$^{-1}$ ($N_3$), no absorption at 663 cm$^{-1}$ for C-Cl.

Preparation of MPEG-DETA (Step 5, Chart A)

MPEG-DAEA 750 was not converted further to the triamine; instead MPEG-diethyltriamine (MPEG-DETA) 5000 was prepared by catalytic hydrogenation of MPEG-DAEA 5000 prepared in the same manner as MPEG-DAEA 750. To 1.0 g of MPEG-DAEA 5000 (0.19 mmoles) was added 125 mg of 10% Pd on carbon in 10 mL of water. The mixture was sparged with $H_2$ with vigorous mixing for 30 hours at atmospheric pressure. The catalyst was then removed by vacuum filtration and 7.5 g of $Na_2SO_4$ added to form two phases. The upper polymer layer was removed, extracted with 10 mL of chloroform/ethanol (1:1.5, v:v), dried over anhydrous $Na_2CO_3$ and precipitated with chilled diethyl ether at 4° C.

The MPEG-DETA is used in metal affinity purification as set forth above for PEG-IDA.

CHART A. MPEG-DETA SYNTHETIC SCHEME

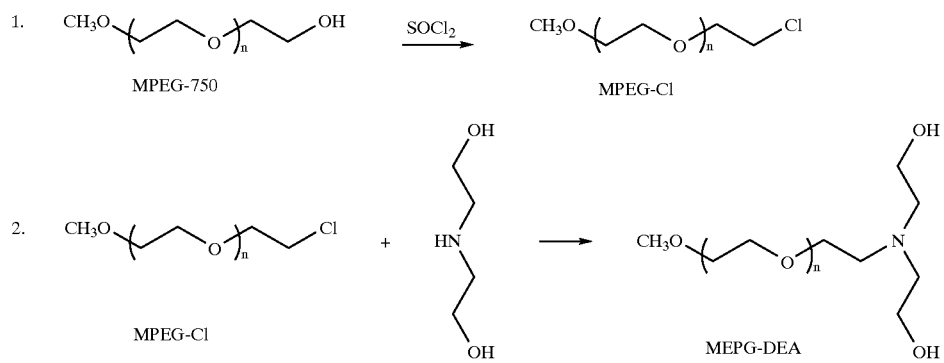

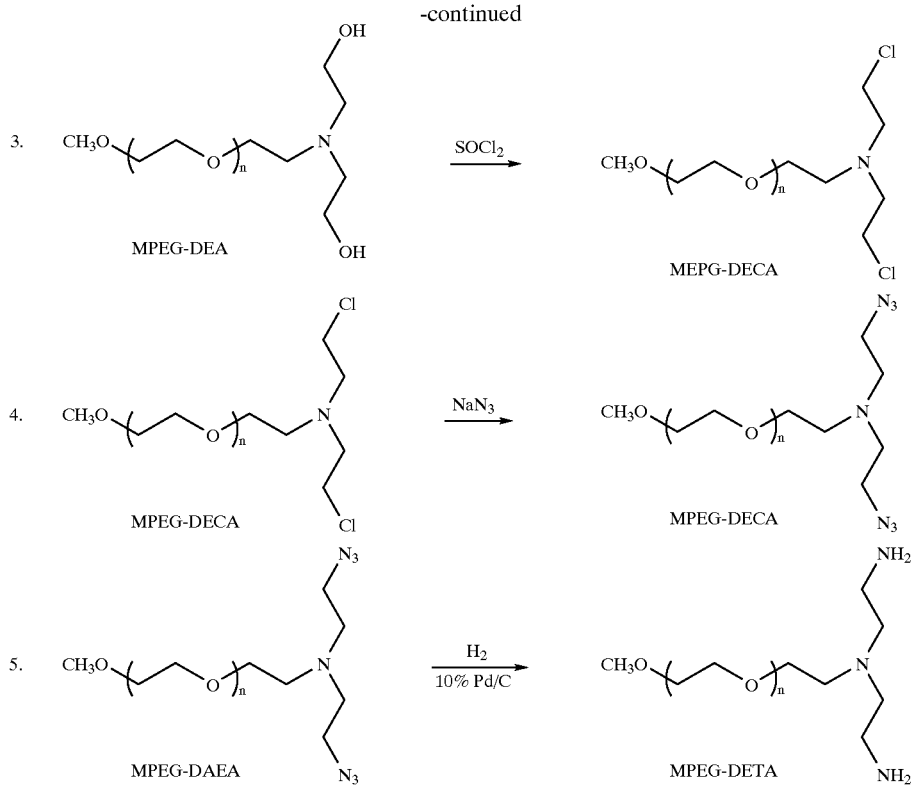

Preparation of the 5000 molecular weight product followed the procedure described for the 750 molecular weight starting material.

In all cases, generally higher isolated yields were obtained for the larger molecular weight intermediates due to their higher melting points and lower solubility in diethyl ether.

Metalation of the MPEG-DETA 5000 product with Cu(II) was unsuccessful and suggests incomplete hydrogenation of the azido groups. Hydrogenation (Step 5) is done as set forth above except that the reactive mixture is hydrogenated at elevated pressure (10–20 psig) for 30 hours to produce the MPEG-DETA for use in subsequent metalation.

Since the direct coupling of DETA to MPEG would inevitably lead to a mixture of substituted amine products, the step-wise synthesis of MPEG-DETA is a novel synthetic approach useful in preparing other potentially useful metal-chelating ligands. This includes the triamino product described in this example as well as bis-substituted PEGs containing multiple chelating groups. The latter, such as the bis-iminodiacetic acid functionalized PEG shown in Chart B, may afford higher selectivity by selective recognition of multiple proximal histidine and cysteine residues found in high affinity metal binding sites and in engineered metal binding sites.

CHART B. BIS-IMINODIACETIC ACID POLY(ETHYLENE GLYCOL)METHYL ETHER

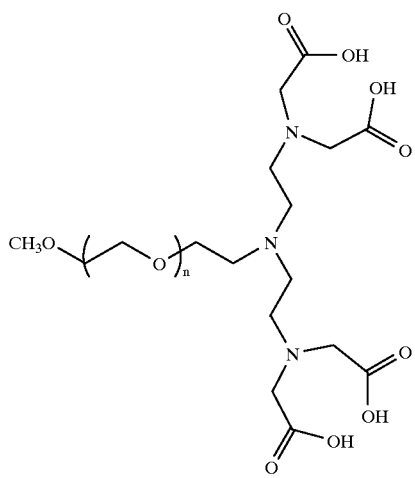

EXAMPLE 11

Metal-Affinity Solubilization of Proteins in Polyethylene Glycol

Precipitation is well known as a method to purify target proteins from mixtures. The selectivity of fractional precipitation schemes can be enhanced by the use of affinity precipitants that function by binding selectively to the desired protein at multiple sites to cause extensive crosslinking and eventually precipitation. On the other hand, keeping the target protein in solution while precipitating unwanted proteins has important processing advantages. Proteins are often damaged during precipitation.

This example sets forth a method of selectively enhancing the solubility of a target protein under conditions leading to the quantitative precipitation of unwanted proteins. The method, called metal affinity solubilization, exploits the reversible binding of a metal-chelator-polymer ligand for acidic amino acid residues on the protein surface. When the protein is bound by a suitable number of polymer ligands, the solubility of the protein in aqueous solutions comprising high concentrations of the same polymer can be greatly enhanced.

Materials and Methods

PEG 4600 was obtained from Sigma (St. Louis) and used without further purification. IDA-PEG 5000 and CU(II) IDA-PEG were prepared from methoxy-PEG 5000 (Sigma) and CuSO4 as set forth in Example 5. Human hemoglobin ($A_o$) was purified from human whole blood as set forth in Example 8.

Solubility Measurements

Stock solutions (0.5 g) containing oxyhemoglobin and buffer were equilibrated at 0–4° C., filtered to 0.2 $\mu$m and combined with systems containing Cu(II)IDA-PEG dissolved in the same buffer to the desired final molar excess of ligand. The stock solutions, containing 11.6 g/L of Hb, were vigorously vortexed and equilibrated at 0–4° C. for 30 minutes. Aliquots from each of these systems were added to samples of 40% PEG 4600 (w/v) to obtain a series of systems (~0.5 g) containing PEG 4600 at a final concentration ranging from 17% to 25%. The systems were vigorously vortexed and incubated at 0–4° C. for 60 minutes followed by centrifugal clarification at 2000 g for 30 minutes. Hb concentrations in the supernatant were measured by absorbance at 412 nm using a millimolar extinction coefficient of 38.2.

The binding of polymer ligands to the protein surface has the effect of reducing the apparent protein solubility in the absence of precipitate. The decrease in hemoglobin solubility was observed at low ionic strength at pH 8. 11. At a pH greater then the isoelectric point of hemoglobin (~7.0) the protein is negatively charged and remains in solution at 30% PEG (w/v). Ligand binding reduces the net protein charge and promotes precipitation. With continued ligand binding, protein precipitation is prevented in the presence of precipitate. The addition of NaCl to the system at pH 8.11 containing no ligand resulted in complete protein precipitation. Decreasing solubility is observed as negative surface charges are neutralized. At a ligand to hemoglobin ratio of 20 complete resolubilization was observed at each PEG concentration.

Copper, like zinc, is known to be an effective protein precipitant because of its ability to coordinate between basic amino acid groups on neighboring proteins. Since precipitation experiments were conducted at 0–4° C. in the absence of reducing agents, the rate of MCO reactions are greatly reduced. In fact, heme oxidation, as measured by the absorbance at 576 nm was completely prevented at reduced temperature. While not wishing to be bound by theory, increasing the number of bound ligands increases the degree to which hydrophobic regions on adjacent proteins are sterically hindered from approaching close enough to initiate aggregation. Sterically hindered aggregation should depend on the number of ligand binding sites, the stability of the ligand-protein complex, the fraction of those sites which are bound and the polymer molecular weight. Furthermore, the locations of those sites are important if they occur near hydrophobic regions on the protein surface. Since the characteristics of each protein in a mixture would differ in terms of these factors this phenomena could be exploited in a method to recover selected proteins from a crude mixture by sterically hindering their aggregation under salting-out conditions.

Metal affinity solubilization is accomplished by adding the metal chelating ligand to a buffered solution (pH 7–8) containing the target protein and other soluble and insoluble cellular components such as contaminating protein, nucleic acids and cell debris. The metal chelating ligand, for example IDA-PEG, metalated with a suitable metal such as Cu(II), Zn(II) or Ni(III) is added to an extent necessary to achieve a sufficient degree of saturation of the binding sites (typically 50–100%). A precipitant is then added to an extent required to achieve precipitation of the undesired soluble components. The precipitant can be poly(ethylene glycol), or other suitable polymer, or a salt such as sodium sulfate, or other salt (except ammonium sulfate) typically used to precipitate proteins. Following separation of the precipitate material, the target protein can be dissociated from the metal chelating ligand by the methods as set forth above.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method for purifying a target protein, comprising:
   (a) obtaining a crude solution of the target protein having at least one surface active electron-rich amino acid;
   (b) adding a salt and a water-soluble hydrophobic molecule to said crude solution to form a two phase aqueous system containing a salt phase and a hydrophobic molecule phase, wherein target protein partitions into the salt phase;
   (c) separating the salt phase from the hydrophobic molecule phase;
   (d) adding a polymer-chelator-metal complex charged with a transition metal ion to said salt phase to form a second two-phase aqueous system comprising a polymer-chelator phase containing said target protein; and
   (e) dissociating the polymer-chelator metal complex from the target protein to obtain purified target protein.

2. The method of claim 1, wherein said water-soluble hydrophobic molecule or said polymer is a polyalkaline oxide.

3. The method of claim 2, wherein said polyalkaline oxide is polypropylene oxide or polyethylene glycol.

4. The method of claim 3, wherein said polyethylene glycol has a molecular weight of about 400 to 20,000.

5. The method of claim 4, wherein said polyethylene glycol has a molecular weight of 1000 to 8000.

6. The method of claim 1, wherein said salt is sodium sulfate, potassium phosphate, ammonium sulfate or magnesium sulfate.

7. The method of claim 1, wherein said salt is magnesium sulfate.

8. The method of claim 1, wherein said transition metal ion is iron, nickel, zinc, cobalt or copper.

9. The method of claim 8, wherein said transition metal ion is copper.

10. The method of claim 1, wherein said chelator is N,N,N'-tris(carboxymethyl)ethylenediamine, iminodiacetic acid, or diethylene triamine.

11. The method of claim 1, wherein said chelator is iminodiacetic acid.

12. The method of claim 1, wherein the polymer-chelator component of said polymer-chelator metal complex is poly (ethylene) methyl ether-diethyltriamine or iminodiacetic acid-polyethylene glycol (IDA-PEG).

13. The method of claim 1, wherein said polymer-chelator-metal complex is Cu(II)IDA-PEG.

14. The method of claim 1, wherein said target protein is hemoglobin.

15. The method of claim 14, wherein said hemoglobin is recombinant hemoglobin.

16. The method of claim 15, wherein said recombinant hemoglobin is a recombinant mutant hemoglobin.

17. The method of claim 15, wherein said recombinant hemoglobin is rHb1.1.

18. The method of claim 1, wherein said polymer-chelator metal complex is dissociated from the protein by lowering the pH, adding a competing electron-donor, or adding a strong chelator.

19. The method of claim 18, wherein said competing electron donor is imidazole or $NH_4Cl$.

20. The method of claim 18, wherein said strong chelator is EDTA.

21. The method of claim 1, wherein said steps (b) and (c) are repeated prior to step (d).

22. The method of claim 1, wherein said amino acid is lysine, arginine, histidine, cysteine, glutamic acid or aspartic acid.

23. The method of claim 22, wherein said amino acid is histidine.

24. The method of claim 22, wherein said amino acid is cysteine.

25. The method of claim 1, wherein said target protein has more than one surface active, electron-rich amino acid.

26. A method of purifying a target protein having a surface active electron-rich amino acid, comprising:

(a) lysing cells containing the target protein to form a crude solution;

(b) adding a salt and a water-soluble hydrophobic molecule to said crude solution to form a two phase aqueous system having a salt phase and a hydrophobic molecule phase, wherein target protein partitions into the salt phase;

(c) separating the salt phase from the hydrophobic molecule phase;

(d) adding a water-soluble hydrophobic molecule to the salt phase to form a second two-phase aqueous solution having a second salt phase and a second hydrophobic molecule phases wherein target protein partitions into the second salt phase;

(e) separating the second salt phase from the second hydrophobic molecule phase;

(f) adding a polymer-chelate-metal complex to said second salt phase to form a polymer-chelate-metal phase and a third salt phase, wherein target protein partitions into the polymer-chelate-metal phase;

(g) disrupting the protein from the polymer-chelate-metal phase to form a phase containing the polymer and a salt phase containing the protein;

(h) separating the salt phase from the polymer phase to obtain purified target protein in the polymer phase.

27. The method of claim 26, comprising the step of further purifying the target protein.

28. A method for purifying a target protein, comprising:

(a) obtaining a crude solution of the target protein having at least one surface active electron-rich amino acid;

(b) adding a salt and a polymer-chelator-metal complex charged with a transition metal ion to form a two-phase aqueous system comprising a polymer-chelator complex phase containing said target protein; and (c) dissociating the polymer-chelator complex from the target protein to obtain purified target protein.

* * * * *